United States Patent [19]

Lorenz, deceased et al.

[11] 4,076,806
[45] Feb. 28, 1978

[54] O-ALKYL-S-[3-OXO-1,2,4-TRIAZOLOBEN-ZOPYRAZIN(2)YL-METHYL]-(THIONO)-THIOLPHOSPHORIC(PHOSPHONIC) ACID ESTERS

[75] Inventors: Walter Lorenz, deceased, late of Wuppertal, Germany, by Erika Lorenz, heiress; Ingeborg Hammann, Cologne, Germany; Bernhard Homeyer, Leverkusen, Germany; Wilhelm Stendel, Wuppertal, Germany

[73] Assignee: Bayer Aktiengesellschaft, Leverkusen, Germany

[21] Appl. No.: 669,781

[22] Filed: Mar. 24, 1976

[30] Foreign Application Priority Data

Apr. 11, 1975 Germany ............................ 2515794

[51] Int. Cl.² .......................... C07F 9/40; C07F 9/165; A01N 9/36
[52] U.S. Cl. .............................. 424/200; 260/250 QP; 260/250 Q
[58] Field of Search .................. 260/250 QP; 424/200

[56] References Cited

PUBLICATIONS

Maki et al. Chem. Abs. 81, 152,214h (1974).

Primary Examiner—R. Gallagher
Assistant Examiner—Mark L. Berch
Attorney, Agent, or Firm—Burgess, Dinklage & Sprung

[57] ABSTRACT

O-Alkyl-S-[3-oxo-1,2,4-triazolobenzopyrazin(2)yl-methyl]-(thiono)thiolphosphoric(phosphonic) acid esters of the formula

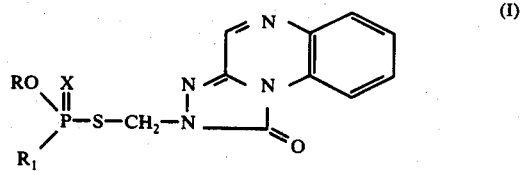

in which
R is alkyl with 1 to 4 carbon atoms,
$R_1$ is alkyl or alkoxy with 1 to 4 carbon atoms, and
X is oxygen or sulfur,
which possess insecticidal properties.

10 Claims, No Drawings

O-ALKYL-S-[3-OXO-1,2,4-TRIAZOLOBEN-ZOPYRAZIN(2)YL-METHYL]-(THIONO)THIOL-PHOSPHORIC(PHOSPHONIC) ACID ESTERS

The present invention relates to and has for its objects the provision of particular new O-alkyl-S-[3-oxo-1,2,4-triazolobenzopyrazin(2)ylmethyl]-(thiono)thiolphosphoric(phosphonic) acid esters, which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from German Pat. Nos. 2,758,115, 2,759,010 and 2,791,599 that O,O-dialkylthiolphosphoric acid esters, for example O,O-dimethyl-S-(ethylthioethyl- (Compound A) and -ethylthionylethyl)-thiolphosphoric acid esters (Compound B) and O,O-diethyl-S-[4-oxo-1,2,3-benzotriazin-3(4H)ylmethyl]-thionothiolphosphoric acid ester (Compound C), have insecticidal properties.

The present invention provides, as new compounds, the S-triazolobenzopyrazinemethyl(thiono)thiolphosphoric(phosphonic) acid esters of the general formula

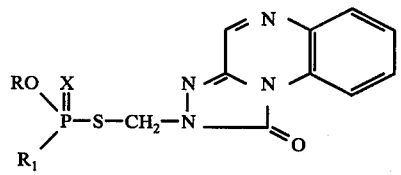

(I)

in which
R is alkyl with 1 to 4 carbon atoms,
$R_1$ is alkyl or alkoxy with 1 to 4 carbon atoms, and
X is oxygen or sulfur.

Preferably, R is straight-chain or branched alkyl with 1 to 3 (especially 1 or 2) carbon atoms, $R_1$ is straight-chain or branched alkyl or alkoxy each with 1 to 3 (especially 1 or 2) carbon atoms, and X is sulfur.

Surprisingly, the S-triazolobenzopyrazinemethyl(thiono)thiolphosphoric(phosphonic) acid esters according to the present invention show a better insecticidal action than the previously known compounds of the same type of action. The compounds according to the invention thus represent a genuine enrichment of the art.

The invention also provides a process for the preparation of an S-triazolobenzopyrazinemethyl(thiono)thiolphosphoric(phosphonic) acid ester of the formula (I) in which a (thiono)thiolphosphoric(phosphonic) acid ester of the general formula

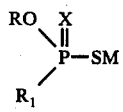

(II), in which
R, $R_1$ and X have the above-mentioned meanings, and
M is hydrogen or one equivalent of an alkali metal, alkaline earth metal or ammonium, is reacted with a 2-halogenomethyl-3-oxo-(1,2,4-triazolobenzopyrazine) of the general formula

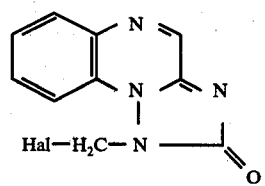

(III), in which
Hal is halogen,
if appropriate in the presence of an acid acceptor and optionally in the presence of a solvent or diluent.

A 2-halogenomethyl-3-oxo-1,2,4-triazolobenzopyrazine to be used as the starting material can be obtained in accordance with generally customary methods, by converting the known-2-hydroxy-benzopyrazine into 2-chloro-benzopyrazine, converting the latter into the hydrazino derivative by means of hydrazine hydrate, and subsequently into the 2-ethoxycarbonylhydrazino derivative. Cyclization in alkaline solution is then carried out, followed by reaction with formaldehyde to give 2-hydroxymethyl-3-oxo-1,2,4-triazolobenzopyrazine and halogenation of the latter, in accordance with the following equations:

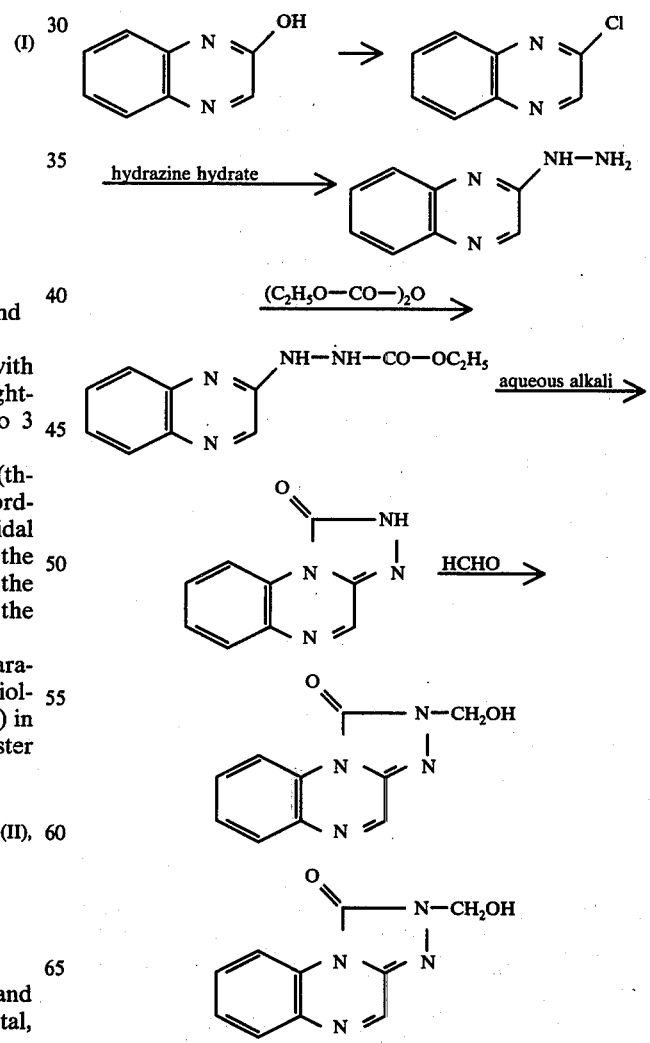

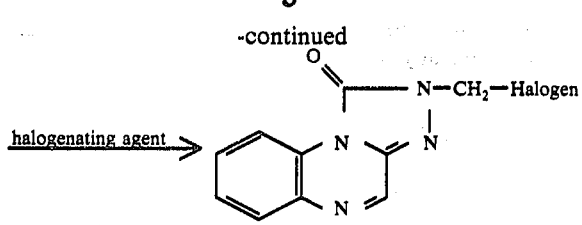

The following may be mentioned as examples of the 2-halogenomethyl-3-oxo-1,2,4-triazolobenzopyrazines to be employed in accordance with the process: 2-chloromethyl- and 2-bromomethyl-3-oxo-1,2,4-triazolobenzopyrazine.

If, for example, the potassium salt of O-ethyl-thiono-thiolethanephosphonic acid ester and 2-chloromethyl-3-oxo-1,2,4-triazolobenzopyrazine are employed as starting materials, the course of the reaction can be represented by the following equation:

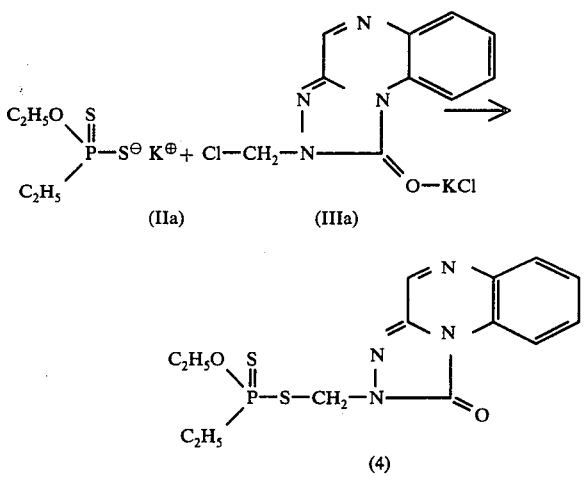

The (thiono)thiolphosphoric(phosphonic) acid esters (II) to be used as starting materials are known from the literature and can be prepared in accordance with generally customary processes.

As examples of these compounds there may be mentioned: O,O-dimethyl-, O,O-diethyl-, O,O-di-isopropyl-, O,O-di-n-propyl-, O-ethyl-O-n-propyl-, O-ethyl-O-isopropyl- and O-methyl-O-ethylthiolphosphoric acid diesters, the corresponding alkali metal salts, alkaline earth metal salts and ammonium salts and, in each case, the corresponding thiono analogues, and also O-methyl-, O-ethyl-, O-n-propyl- and O-isopropyl- methane-, -ethane-, -n-propane- and -isopropane-thiolphosphonic acid esters, the corresponding alkali metal salts, alkaline earth metal salts and ammonium salts and, in each case, the corresponding thiono analogues.

The process for the preparation of the compounds according to the invention is preferably carried out in the presence of a suitable solvent or diluent. Practically all inert organic solvents can be employed for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate, methylate and ethylate and potassium carbonate, methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at from 40° to 50° C.

The reaction is in general allowed to take place under normal pressure.

To carry out the process, the 2-halogenomethyl-3-oxo-1,2,4-triazolobenzopyrazine is preferably employed in 10 to 20% excess. In most cases, the (thiono)thiolphosphoric (phosphonic) acid ester component is employed in the form of a salt. After bringing the components together, preferably in a solvent or diluent, the reaction solution is stirred at an elevated temperature for one or more hours. After completion of the reaction, the solution is filtered while still warm, the solvent is distilled off and water is added to the residue. In some cases, the substance which separates out can be filtered off directly; in other cases, the aqueous phase is extracted by shaking with an organic solvent, for example toluene, and the organic layer is worked up in the usual manner by washing, drying and distillation. Most substances are obtained in a crystalline form and are characterized by their melting point. Some are obtained in the form of oils which in most cases cannot be distilled without decomposition but are freed from the last volatile constituents by so-called "slight distillation", that is to say by prolonged heating to moderately elevated temperatures under reduced pressure, and are purified in this way. They are characterized by the refractive index.

As has already been mentioned, the S-triazolobenzopyrazinemethyl(thiono)thiolphosphoric(phosphonic) acid esters according to the invention are distinguished by an excellent insecticidal activity. They are active not only against leaf insects and soil insects and against pests harmful to health and pests of stored products, but also, in the veterinary medicine field, against animal parasites (ectoparasites), such as parasitic fly larvae. They combine a low phytotoxicity with a good action against both sucking and biting insects.

For this reason, the compounds according to the invention can be employed successfully as pesticides in plant protection as well as in the hygiene field, the field of protection of stored products and the veterinary field.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the mealy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the cotton bug (*Dysdercus intermedius*), the bed bug (*Cimex lectularius*), the assassin bug (*Rhodnius*

*prolixus*) and Chagas' bug (*Triatoma infestans*) and, further, cicadas, such as *Euscelis bilobatus and Nephotettix bipunctatus.*

In the case of the biting insects, above all there should be mentioned butterfly caterpillars (Lepidoptera) such as the diamond-back moth (*Plutella maculipennis*) the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), Oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, which comprises applying to at least one of correspondingly (a) such insects, and (b) the corresponding habitat thereof, i.e. the locus to be protected, e.g. to a growing crop, to an area where a crop is to be grown or to a domestic animal, a correspondingly combative or toxic amount, i.e. an insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon Larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all of the beetle larvae had been killed whereas 0% means that none of the beetle larvae has been killed.

The active compounds, the concentrations of the active compounds, the evaluation times and the results can be seen from the following table:

Table 1

(*Phaedon* larvae test)

| Active compound | Active compound concentration in % | Degree of destruction in % after 3 days |
|---|---|---|
| $C_2H_5-S-CH_2-CH_2-S-\overset{O}{\overset{\|}{P}}(OCH_3)_2$ (known) (A) | 0.1<br>0.01<br>0.001 | 100<br>100<br>0 |
| $C_2H_5-\overset{O}{\overset{\|}{S}}-CH_2-CH_2-S-\overset{O}{\overset{\|}{P}}(OCH_3)_2$ (known) (B) | 0.1<br>0.01<br>0.001 | 100<br>100<br>0 |
| benzo-triazinone-CH$_2$-S-P(OCH$_3$)$_2$ (3) | 0.1<br>0.01<br>0.001 | 100<br>100<br>100 |
| benzo-triazinone-CH$_2$-S-P(OC$_2$H$_5$)$_2$ (2) | 0.1<br>0.01<br>0.001 | 100<br>100<br>90 |

Table 1-continued
(Phaedon larvae test)

| Active compound | Active compound concentration in % | Degree of destruction in % after 3 days |
|---|---|---|
| Compound (1): quinoxaline ring fused with N-C(=O)-N-CH₂-S-P(=O)(OCH₃)₂ | 0.1 | 100 |
| | 0.01 | 100 |
| | 0.001 | 95 |

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified period of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 2
(Plutella test)

| Active compound | Active compound concentration in % | Degree of destruction in % after 3 days |
|---|---|---|
| $C_2H_5S-CH_2-CH_2-S-P(=O)(OCH_3)_2$ (known) (A) | 0.1 | 100 |
| | 0.01 | 0 |
| $C_2H_5-S(=O)-CH_2-CH_2-S-P(=O)(OCH_3)_2$ (known) (B) | 0.1 | 100 |
| | 0.01 | 0 |
| Compound (3): quinoxaline-N-C(=O)-N-CH₂-S-P(=S)(OCH₃)₂ | 0.1 | 100 |
| | 0.01 | 100 |
| Compound (1): quinoxaline-N-C(=O)-N-CH₂-S-P(=O)(OCH₃)₂ | 0.1 | 100 |
| | 0.01 | 100 |
| Compound (2): quinoxaline-N-C(=O)-N-CH₂-S-P(=S)(OC₂H₅)₂ | 0.1 | 100 |
| | 0.01 | 100 |
| Compound (4): quinoxaline-N-C(=O)-N-CH₂-S-P(=S)(OC₂H₅)(C₂H₅) | 0.1 | 100 |
| | 0.01 | 100 |

EXAMPLE 3

Critical concentration test/soil insects

Test insect: *Phorbia antigua* grubs in the soil

Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectivenes of the active compound was determined in % by counting the dead and live test insects. The degree of effectiveness is 100% if all test insects has been killed and is 0% if exactly as many test insects were still alive as in the case of the untreated control.

The active compounds, amounts used and results can be seen from the table which follows:

Table 3

(Soil insecticide test/*Phorbia antiqua* grubs in the soil)

| Active compound | Degree of destruction in % at an active compound concentration of 20 ppm |
|---|---|
| $C_2H_5S-CH_2-CH_2-S-\overset{\overset{O}{\|}}{P}(OCH_3)_2$ (known) (A) | 0 |
| $C_2H_5-\overset{\overset{O}{\|}}{S}-CH_2-CH_2-S-\overset{\overset{O}{\|}}{P}(OCH_3)_2$ (known) (B) | 0 |
| 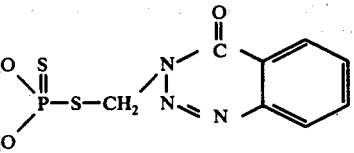 (2) | 100 |
| 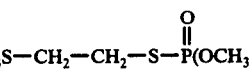 (4) | 100 |

EXAMPLE 4

Critical concentration test/soil insects

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all the test insects had been killed and is 0% if exactly as many test insects were still alive as in the case of the untreated control.

The active compounds, amounts used and results can be seen from the table which follows:

Table 4

(Soil insecticide test/*Tenebrio molitor* larvae in the soil)

| Active compound | Degree of destruction in % at an active compound concentration of 20 ppm |
|---|---|
| 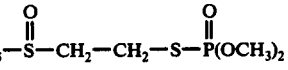 (known) (C) | 50 |
| $C_2H_5S-CH_2-CH_2-S-\overset{\overset{O}{\|}}{P}(OCH_3)_2$ (known) (A) | 0 |
| $C_2H_5-\overset{\overset{O}{\|}}{S}-CH_2-CH_2-S-\overset{\overset{O}{\|}}{P}(OCH_3)_2$ (known) (B) | 0 |
| 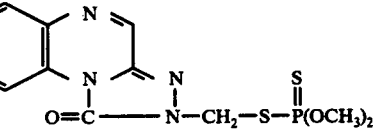 (3) | 100 |
| 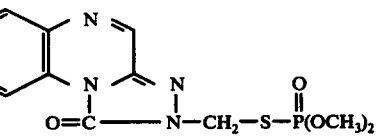 (1) | 100 |

EXAMPLE 5

Test with parasitic fly larvae

Solvent:
  35 parts by weight of ethylene polyglycol monomethyl ether
  35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina* res.) were introduced into a test tube which contained approximately 2 cm³ of horse muscle. 0.5 ml of the preparation of active compound was applied to this horse meat. After 24 hours, the degree of destruction in % was determined. 100% means that all the larvae had been killed and 0% means that no larvae had been killed.

The active compounds investigated, the concentrations of the active compounds used and the results obtained can be seen from the table which follows:

Table 5

| (Test with parasitic fly larvae/*Lucilia cuprina* res.) | | |
|---|---|---|
| Active compound | Active compound concentration in ppm | Degree of destruction in % |
| (2) | 100 | 100 |
|     | 10  | 100 |
| (3) | 100 | 100 |
|     | 30  | 100 |
|     | 10  | 100 |
|     | 1   | 100 |
| (1) | 100 | 100 |
|     | 10  | 100 |
|     | 1   | 100 |
| (4) | 100 | 100 |
|     | 30  | 100 |
|     | 10  | 100 |
| (5) | 100 | 100 |
|     | 10  | 100 |
|     | 1   | 100 |

The process of this invention is illustrated by the following preparative Examples.

EXAMPLE 6

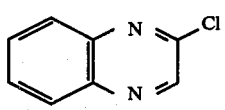
(a)

A mixture of 74 g (0.5 mole) of 2-hydroxy-benzopyrazine, 12 g of dimethylaniline and 250 ml of phosphorus oxychloride was heated under reflux for 10 minutes. At about 80° C, all the material had dissolved; the reaction solution was cooled and poured onto ice, and the product was filtered off. The residue was dried on clay and was then taken up in petroleum ether, and the solution was filtered through active charcoal. The reaction solution was evaporated and 78 g (87.5% of theory) of 2-chloro-benzopyrazine of melting point 48°-49° C, were obtained.

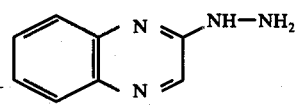
(b)

165 g (1 mole) of the substance described under (a) were added to a mixture of 400 ml of absolute ethanol and 400 ml of hydrazine hydrate and the reaction temperature was kept at 40° C by slight cooling. The mixture was stirred for a further 3 hours and the precipitate was filtered off and washed with water. 137 g (85.5% of the theory) of 2-hydrazino-benzopyrazine, of melting point 162° C (decomposition) were obtained as an orange-colored powder.

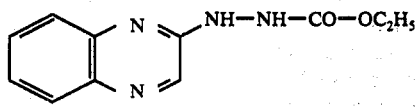
(c)

152 g (0.96 mole) of pyrocarbonic acid diethyl ester were added to 128 g (0.8 mole) of 2-hydrazino-benzopyrazine in 2 l of dry ethanol and the reaction solution was kept at 35° C by slight cooling. After the evolution of $CO_2$ had ended, a product crystallized out. The reaction mixture was stirred for a further 30 minutes and the product was then filtered off. 165 g (88.5% of theory) of 2-(2'-ethoxycarbonylhydrazino)-benzopyrazine were obtained as a yellow powder of decomposition point 180°–190° C.

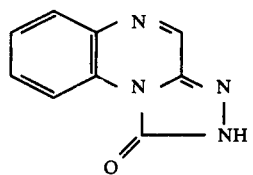
(d)

138 g (0.6 mole) of the substance prepared under (c) were added to 265 g (0.66 mole) of sodium hydroxide in 660 ml of water. The reaction mixture was left to stand on a waterbath for 3 hours at 80° C. The turbid solution was filtered hot, cooled and acidified and the precipitate was filtered off. 101 g (90% of theory) of 3-oxo-1,2,4-triazolo-2H-benzopyrazine of melting point 298° C were obtained as a yellow, non-crystallizable powder.

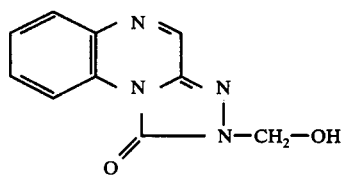
(e)

A mixture of 560 ml of formaldehyde and 93 g of 3-oxo-1,2,4-triazolo-2H-benzopyrazine was warmed on a water bath. The mixture thickened initially and then again became somewhat less viscous. The reaction mixture was left to stand for 2 hours at 80° C and was then cooled, and the precipitate was filtered off and washed with water. 99 g (91.5% of theory) of 2-hydroxymethyl-3-oxo-1,2,4-triazolo-benzopyrazine were obtained as a yellow powder of melting point 204° C (decomposition).

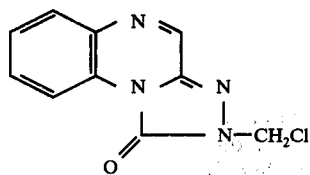
(f)

68.5 g (0.48 mole; 42 ml) of thionyl chloride were added to a mixture of 86.5 g (0.4 mole) of 2-hydroxymethyl-3-oxo-1,2,4-triazolo-benzopyrazine in 400 ml of methylene chloride and 2 ml of dimethylformamide, while keeping the reaction temperature at 35° C by slight cooling. After stirring for 2 hours, the reaction mixture was subjected to distillation and water was added to the residue. The aqueous solution was rendered neutral with sodium bicarbonate and the product was filtered off. This gave 90 g (95.5% of theory) of 2-chloromethyl-3-oxo-1,2,4-triazol benzopyrazine of melting point 178° C. The yellow crystals could be recrystallized from acetonitrile.

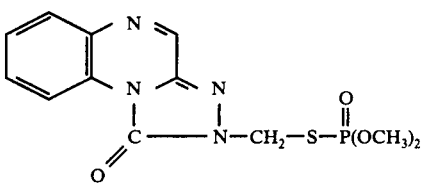
(g) (1)

70 g (0.3 mole) of 2-chloromethyl-3-oxo-1,2,4-triazolobenzopyrazine were added to 57 g (0.36 mole) of the ammonium salt of O,O-dimethylthiolphosphoric acid ester in 350 ml of acetonitrile and the reaction solution was stirred for 2 hours at 50° C. The solution was filtered while warm, the solvent was distilled off and water was added to the residue. The mixture was again filtered, the product was recrystallized from acetone and 32 g (31.5% of theory) of O,O-dimethyl-S-[3-oxo-1,2,4-triazolobenzopyrazin(2)ylmethyl]-thiolphosphoric acid ester were obtained in the form of fine yellow crystals of melting point 125° C.

EXAMPLE 7

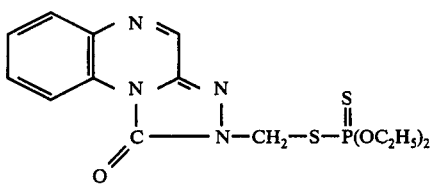
(2)

70 g (0.3 mole) of 2-chloromethyl-3-oxo-1,2,4-triazolobenzopyrazine were added to 73 g (0.36 mole) of the ammonium salt of O,O-diethylthionothiolphosphoric acid diester, dissolved in 300 ml of acetone; there was no exothermic effect. After stirring for one hour at 50° C, the reaction mixture was cooled and filtered, and the solvent was distilled off. Water was added to the residue and the product was filtered off and taken up in toluene. The organic phase was dried and the solvent was distilled off. 97 g (84% of theory) of O,O-diethyl-S-[3-oxo-1,2,4-triazolobenzopyrazine(2)ylmethyl]-thionothiolphosphoric acid ester were obtained. The substance was recrystallized from acetonitrile; yellow needles of melting point 100° C were obtained.

The following compounds can be prepared by analogous procedures:

| Compound No. | Structure | Physical data (melting point [° C]; refractive index) | Yield (% of theory) |
|---|---|---|---|
| (3) | 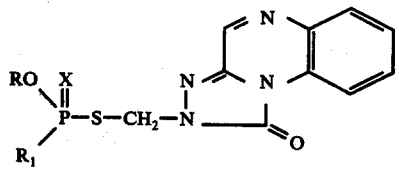 | 123 | 60.5 |
| (4) | 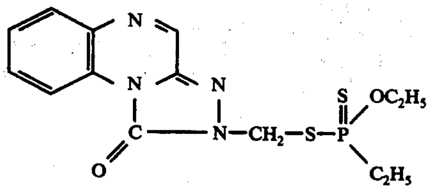 | 122 | 80 |
| (5) | 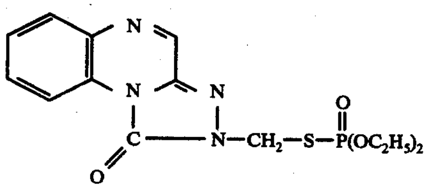 | $n_D^{21}$: 1.5890 | 45 |

It will be appreciated that the instant specification and examples are set forth by way of illustration and not limitation, and that various modifications and changes may be made without departing from the spirit and scope of the present invention.

What is claimed is:

1. An O-alkyl-S-[3-oxo-1,2,4-triazolobenzopyrazin-(2)ylmethyl]-(thiono)thiolphosphoric(phosphonic) acid ester of the formula in which
R is alkyl with 1 to 4 carbon atoms,
$R_1$ is alkyl or alkoxy with 1 to 4 carbon atoms, and
X is oxygen or sulfur.

2. A compound according to claim 1, in which R is straight-chain or branched alkyl with 1 to 3 carbon atoms, $R_1$ is straight-chain or branched alkyl or alkoxy with 1 to 3 carbon atoms, and X is sulfur.

3. The compound according to claim 1, wherein such compound is O,O-dimethyl-S-[3-oxo-1,2,4-triazolobenzopyrazin(2)ylmethyl]-thiolphosphoric acid ester of the formula

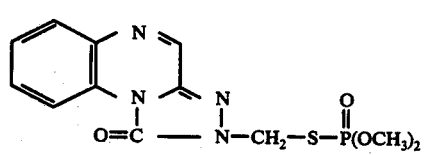

4. The compound according to claim 1, wherein such compound is O,O-diethyl-S-[3-oxo-1,2,4-triazolobenzopyrazin-(2)ylmethyl]-thionothiolphosphoric acid ester of the formula

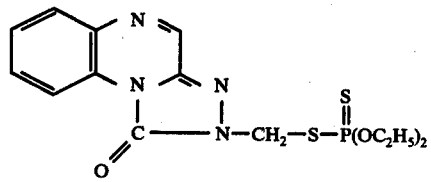

5. The compound according to claim 1, wherein such compound is O,O-dimethyl-S-[3-oxo-1,2,4-triazolobenzopyrazin-(2)ylmethyl]-thionothiolphosphoric acid ester of the formula

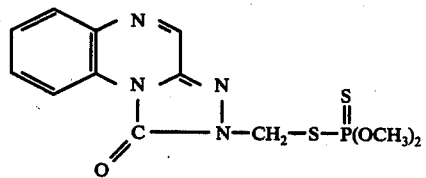

6. The compound according to claim 1, wherein such compound is O-ethyl-S-[3-oxo-1,2,4-triazolobenzopyrazin(2)yl-methyl]-ethanethionothiolphosphonic acid ester of the formula

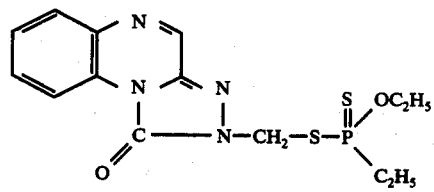

7. The compound according to claim 1, wherein such compound is O,O-diethyl-S-[3-oxo-1,2,4-triazolobenzopyrazin-(2)ylmethyl]-thiolphosphoric acid ester of the formula

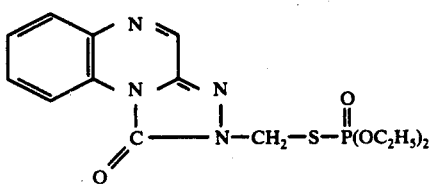

8. An insecticidal composition containing as active ingredient an insecticidally effective amount of a compound according to claim 1 in admixture with a pesticide diluent.

9. A method of combating insects which comprises applying to the insects or an insect habitat an insecticidally effective amount of a compound according to claim 1.

10. The method according to claim 9 in which said compound is
O,O-dimethyl-S-[3-oxo-1,2,4-triazolobenzopyrazin(2-)yl-methyl]-thiolphosphoric acid ester,
O,O-diethyl-S-[3-oxo-1,2,4-triazolobenzopyrazin(2-)ylmethyl]-thionothiolphosphoric acid ester,
O,O-dimethyl-S-[3-oxo-1,2,4-triazolobenzopyrazin(2-)yl-methyl]-thionothiolphosphoric acid ester,
O-ethyl-S-[3-oxo-1,2,4-triazolobenzopyrazin(2)ylmethyl]-ethanethionothiolphosphonic acid ester, or
O,O-diethyl-S-[3-oxo-1,2,4-triazolobenzopyrazin(2-)yl-methyl]-thiolphosphoric acid ester.

* * * * *